(12) United States Patent
Nichols et al.

(10) Patent No.: US 6,395,263 B1
(45) Date of Patent: *May 28, 2002

(54) SMEAR-RESISTANT COSMETIC

(75) Inventors: Rosemarie Nichols, 205 38th Pl., Manhattan Beach, CA (US) 90266; Martin J. Weisman, Westlake Village, CA (US)

(73) Assignee: Rosemarie Nichols, Manhattan Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/665,885

(22) Filed: Sep. 20, 2000

Related U.S. Application Data

(63) Continuation of application No. 09/472,355, filed on Dec. 23, 1999, now Pat. No. 6,203,809, which is a continuation of application No. 09/266,469, filed on Mar. 11, 1999, now Pat. No. 6,027,739, which is a division of application No. 08/647,837, filed on May 15, 1996, now Pat. No. 6,001,374, and a continuation-in-part of application No. 08/440,780, filed on May 15, 1995, now Pat. No. 5,747,017.

(51) Int. Cl.$^7$ .............................. A61K 6/00; A61K 7/00; A61K 7/025
(52) U.S. Cl. ........................................ 424/64; 424/401
(58) Field of Search .................................. 424/401, 64

(56) References Cited

U.S. PATENT DOCUMENTS

| | | | | |
|---|---|---|---|---|
| 2,230,063 A | * | 1/1941 | Klimist ........................ 167/85 |
| 2,566,722 A | | 9/1951 | Friedberg .................... 91/54.7 |
| 3,646,214 A | | 2/1972 | Katz ........................... 424/362 |
| 3,927,199 A | | 12/1975 | Micchelli et al. ............. 424/47 |
| 4,192,861 A | | 3/1980 | Micchelli et al. ............. 424/47 |
| 4,283,384 A | | 8/1981 | Jacquet et al. ................ 424/47 |
| 4,315,910 A | | 2/1982 | Nowak, Jr. et al. ........... 424/47 |
| 4,409,203 A | | 10/1983 | Gordon et al. ................ 424/61 |
| 4,421,881 A | | 12/1983 | Benkendorf et al. .......... 524/24 |
| 4,534,961 A | | 8/1985 | Liff .............................. 424/63 |
| 4,601,757 A | | 7/1986 | Brown et al. ................ 106/183 |
| 4,649,045 A | | 3/1987 | Gaske et al. .................. 424/61 |
| 4,699,780 A | * | 10/1987 | Jennings et al. .............. 424/60 |
| 4,747,419 A | | 5/1988 | Flynn et al. .................. 132/73 |
| 4,795,631 A | * | 1/1989 | Sheehan ....................... 424/64 |
| 4,897,261 A | | 1/1990 | Yamazaki et al. ............. 424/61 |
| 4,904,698 A | | 2/1990 | Adkins, Jr. et al. ......... 514/642 |
| 4,935,228 A | | 6/1990 | Finkenaur et al. ............. 424/64 |
| 4,980,167 A | | 12/1990 | Harashima et al. .......... 424/401 |
| 5,045,309 A | | 9/1991 | Dell'Aquila .................. 424/61 |
| 5,085,855 A | | 2/1992 | Shore ........................... 424/64 |
| 5,085,856 A | * | 2/1992 | Dunphy et al. ............... 424/64 |
| 5,093,108 A | | 3/1992 | Pappas et al. ................. 424/61 |
| 5,093,111 A | | 3/1992 | Baker et al. .................. 424/64 |
| 5,106,609 A | | 4/1992 | Bolich, Jr. et al. ............ 424/70 |
| 5,108,736 A | | 4/1992 | Schlossman .................. 424/64 |
| 5,143,723 A | * | 9/1992 | Calvo et al. .................. 424/63 |
| 5,238,678 A | | 8/1993 | Shiozawa et al. ............. 424/63 |
| 5,288,493 A | | 2/1994 | Martino et al. .............. 424/401 |
| 5,505,937 A | | 4/1996 | Castrogiovanni et al. ..... 424/64 |
| 5,665,364 A | | 9/1997 | McAtee et al. .............. 424/401 |
| 5,747,017 A | | 5/1998 | Nichols et al. ................ 424/61 |
| 6,001,374 A | * | 12/1999 | Nichols ....................... 424/401 |
| 6,010,709 A | | 1/2000 | Nichols ....................... 424/401 |
| 6,027,739 A | * | 2/2000 | Nichols ....................... 424/401 |

FOREIGN PATENT DOCUMENTS

| | | |
|---|---|---|
| EP | 0005922 | 5/1979 |
| FR | 2638636 | 11/1988 |
| WO | WO 86/02001 | 4/1986 |
| WO | WO 92/19215 | 11/1992 |

OTHER PUBLICATIONS

Wilkinson, J.B. and Moore, R.J. eds. (1982) "Harry's Cosmeticology, 7th edition." Chemical Publishing, New York pp. 332–333.

Janistyn, Von Hugo (1966) "Taschenbuch Der Mernen Parfumerie Und Kosmetik." Wiseenschafltiche Verlagsgesellschaft M.B.H., Stutgart p. 609.

United States District Court, Central District of California, Western Division Defendants' Answer and Counterclaims in Response to Plaintiff's Second Amended Complaint, Case No. CV–00–6376 CM (Ex).

United States District Court, Central District of California, Western Division Defendants Senegence International's Response to Plaintiffs' Second Set of Interrogatories Nos. 5–15. Case No. CV–00–6376 CM (Ex).

United States District Court, Central District of California, Western Division Defendant 220 Laboratories Inc.'s Responses to Plaintiff's Second Set of Interrogatories (Nos. 6–14). Case No. CV–00–6376 CM (Ex).

United States District Court, Central District of California, Western Division Defendants Senegence International's Response to Plaintiffs' First Set of Requests for Admissions Nos. 1–300. Case No.: CV–00–6376 CM (Ex).

United States District Court, Central District of California, Western Division Defendants Senegence International's Response to Plaintiffs' Second Set of Requests for Admissions Nos. 301–309. Case No.: CV–00–6376 CM (Ex).

(List continued on next page.)

*Primary Examiner*—Thurman K. Page
*Assistant Examiner*—S. Howard
(74) *Attorney, Agent, or Firm*—Barnes & Thornburg; Alice O. Martin

(57) ABSTRACT

A cosmetic which includes from about one to about ten parts ethyl cellulose, from about one to about ten parts of a cosmetic pigment, from about 70 to about 95 parts of an organic solvent, and from about one to about ten parts of an alcohol soluble and water insoluble resin. The resin is a polymer which includes one or more of the following monomers: octylacrylamide, acrylate, butylaminoethyl methacrylate, and methyl methacrylate, hydroxypropyl methacrylate, polyvinyl acetate.

15 Claims, No Drawings

OTHER PUBLICATIONS

United States District Court, Central District of California, Western Division Defendant 220 Laboratories Inc.'s Responses to Plaintiffs' First Set of Requests for Admissions Nos. 1–300. Case No. CV–00–6376 CM (Ex).

United States District Court, Central District of California, Western Division Defendants'Notice of Motion and Motion for Summary Judgement of Noninfringement of U.S. Pat. No. 6,207,739. Case No. CV–00–6376 CM (Ex).

United States District Court, Central District of California, Western Division Defendants'Notice of Motion and Motion for Summary Judgement of Noninfringement of U.S. Pat. No. 6,001,374. Case No. CV–00–6376 CM (Ex).

Amphomer, "Polymer for Hard Holding Hair Fixative Formulations: National Starch and Chemical Company, Specialty Polymers".

Harry's Cosmeticology, "Coloured Make–up Preparation", pp. 332–333, 7th Edition, Chemical Publishing Co. 1982.*

* cited by examiner

SMEAR-RESISTANT COSMETIC

RELATED APPLICATIONS

This application is a continuation of U.S. patent application Ser. No. 09/472,355, filed Dec. 23, 1999, now U.S. Pat. No. 6,203,809 the disclosure of which is incorporated herein by reference in its entirety, which is a continuation of U.S. patent application Ser. No. 09/266,469, filed Mar. 11, 1999, now U.S. Pat. No. 6,027,739, which was a divisional of application Ser. No. 08/647,837, filed May 15, 1996, now U.S. Pat. No. 6,001,374. Application Ser. No. 08/647,837 is a continuation in part of application Ser. No. 08/440,780, filed May 15, 1995, now U.S. Pat. No. 5,747,017.

BACKGROUND OF THE INVENTION

1. Field of the Invention

The present invention relates to a kits, methods, and compositions for enhancing the appearance of the lips. The invention contemplates cosmetic compositions for applying the color to the lips, compositions for enhancing the finish the finish of the cosmetic, color enhancing powders, and formulations for removing the color. Kits containing the above compositions are also contemplated. The present invention also relates to methods of using the preceding compositions.

2. Description of the Prior Art

For many years, lipstick has been utilized as a cosmetic preparation for heightening or altering the color of the lips. Conventional lipstick is formed by a cosmetic coloring in a wax carrier. Although lipstick has many disadvantages, there has thus far been no suitable alternative.

The lipsticks which have heretofore been available have the marked disadvantage of being readily transferable from a person's lips to other objects. Lipstick smears and rubs off while swimming, smoking, kissing, or by any other contact of the lips with articles such as coffee cups, tea cups, napkins and clothing. This leads to the loss of the lipstick application when drinking beverages, when swimming, and even when in engaging in none of these activities due simply to licking the lips. Thus, while lipstick is normally initially applied in a relatively even application across the externally exposed areas of the lips, the application of lipstick will readily dissipate and assumes a nonuniform coverage. The greatest loss of the lipstick application is typically near the portions of the lips closest to a person's mouth. As a consequence, it is necessary to frequently reapply layers of lipstick in order to maintain a uniform coverage of a lipstick application on a person's lips. This frequent necessity for reapplication aggravates a further disadvantage of conventional lipstick.

Lipstick has the additional disadvantage of being susceptible to cracking and caking. This disadvantage is particularly pronounced when several layers of lipstick have been applied to attempt to replenish a lipstick application that has been lost due to transfer to other articles. As a consequence, the frequent reapplication of lipstick results in perceptible cracking and calling of the lipstick covering a person's lips. Caking and cracking of a lipstick application detracts from the natural appearance of the lips and is aesthetically undesirable.

Attempts have been made over the years to provide alternative cosmetic which do not entail the disadvantages of lipstick. For example, U.S. Pat. No. 2,230,063 describes a liquid lip rouge preparation which employs a combination of ethyl cellulose and wax-free shellac as film-forming materials. However, shellac does tend to crack. Heretofore, no suitable alternative to lipstick has been found.

SUMMARY OF THE INVENTION

The present invention is an innovative new alternative to lipstick. The cosmetic of the present invention does not take the form of a gooey stick, but rather is a unique, smear-proof and waterproof liquid that dries quickly to an extremely sheer, soft finish that feels remarkably like bare skin. In one embodiment, the cosmetic comprises between about 0.1 and about 20 parts of an alcohol soluble and water insoluble resin, between about 0.1 and about 15 parts of a cellulose, between about 0.1 and about 15 parts of a cosmetic pigment, and between about 50 and 99 parts of an organic solvent.

The cosmetic of the present invention is both smear-proof and waterproof. It will not streak, smear, or rub off while swimming, smoking, or kissing. Use of the cosmetic of the present invention avoids the disadvantages of stains on coffee cups, cheeks and collars. The cosmetic of the present invention has twice the staying power of lipsticks which purport to be waterproof or kiss-proof The cosmetic of the present invention has further advantages in that it won't stick to dental work or braces. It can also be used on hair or eyebrows, as well as to cover any bald areas on the head. It can be used to cover scars or tattoos anywhere on the body.

The present invention provides a perfect cosmetic for busy professional women. It is highly advantageous for wear at weddings, parties, for use at the beach, for use while skiing and for wear during all active sports. The cosmetic of the invention is extremely attractive and can be worn at important dinner dates, as well as during informal events. The wearer can even sleep or shower while wearing the cosmetic, since it will not fade or smear under such circumstances. The user may apply several layers of the cosmetic to achieve the desired appearance.

The present invention also relates to compositions for enhancing the finish of the cosmetic. Such compositions, when applied over the cosmetic, transform the finish of the cosmetic from a matte to a high-gloss finish. The finish enhancing compositions also keep the lips soft and moist and may be massaged lightly into the lips prior to application of the cosmetic to condition and moisturize the lips. The finish enhancing compositions may be applied with an applicator wand. The user can apply the finish enhancing composition multiple times, whenever it is desired to moisturize the lips or to enhance the finish of the cosmetic.

The appearance of the lips can be further enhanced using color enhancing compositions comprising a colorant powder, which may be supplied in pressed or loose form. The colorant powder may be supplied in a compact and can be gently pressed onto the cosmetic using a brush. The colorant powders may also be used as a foundation base or may be applied between the second and third layers of the cosmetic. The visual effect of the colorant powders may be moderated by applying the finish enhancing composition over the colorant powder.

The present invention also relates to compositions for removing the cosmetic, finish enhancer, and color enhancers. These compositions may be dabbed on a tissue and applied to the lips when the user desires to remove the preceding compositions from the lips.

The present invention also relates to kits comprising the preceding compositions and to methods of using the preceding compositions.

DETAILED DESCRIPTION OF THE PREFERRED EMBODIMENTS

In one broad aspect, the invention may be considered to be a cosmetic comprising between about 0.1 and about 20 parts of an alcohol soluble and water insoluble resin, between about 0.1 and about 15 parts ethyl cellulose, between about 0.1 and about 15 parts of a cosmetic pigment, and between about 50 and about 99 parts of an organic solvent. All parts used herein are percent by weight.

Preferentially, the solvent is denatured alcohol. In a preferred version the alcohol soluble and water insoluble resin is present in between about one and about 10 parts. In a further preferred embodiment, the ethylcellulose is present in between about 1 and about 10 parts. In a further preferred embodiment, the cosmetic pigment is present in between about 2 and about 10 parts.

In another broad aspect, the invention may be considered to be an improvement in a cosmetic employing a coloring agent and a plasticizer in a volatile solvent. The improvement is comprised of at least one film-forming agent present in an amount of at least about one percent wherein the film-forming agent is selected from the group consisting of: AMPHOMER (copolymers of N-tert-octylacrylamide, methyl methacrylate, hydroxypropylmethacrylate, acrylic acid and/or t-butyl aminoethylmethacrylate), AMPHOMER LOVOCRYL-47 (an octylacrylamide/acrylateibutylaminoethyl methacrylate copolymer), Carboset, JONCRYL (styrene/acrylate copolymers), QUADAMER (terpolymers of alkyl acrylamide, acrylamide or methacrylamide, N-vinyl pyrrolidone, and acrylic or methyacrylic acid), GANTREZ ( copolymers of vinyl methyl ether and monoalkyl esters of maleic anhychide), and polyvinyl acetate copolymers.

In yet another broad aspect, the invention may be considered to be an improvement in a cosmetic employing a pigment and a film-forming agent in an organic solvent carrier. According to the improvement of the invention, the film-forming agent includes an alcohol soluble and a water insoluble substance present in an amount of at least about one percent and selected from the group consisting of AMPHOMER, AMPHOMER LOVOCRYL-47, Carboset, JONCRYL, QUADAMER, GANTREZ and polyvinyl acetate copolymers.

The critical component of the invention is the alcohol soluble and water insoluble resin. A number of different resins of the type may be employed in formulating the cosmetic of the invention. The alcohol soluble, water insoluble resin may be selected from the group consisting of octylacrylamides, acrylates, butylaminoethyl methacrylate copolymers and polyvinyl acetate copolymers. The alcohol soluble, water insoluble resin or mixture of resins serves as a vital component of the film-forming agent. This film-forming agent may be selected from the group consisting of: AMPHOMER, AMPHOMER LOVOCRYL-47, Carboset, JONCRYL, QUADAMER, GANTREZ and polyvinyl acetate copolymers. Five performance tests were conducted on a variety of resins to determine their suitability for use in the present cosmetics. The suspension test was employed to assess the ability of the test compound to be solubilized in a solution of 4.4% test resin, 3.5% ethyl cellulose, 0.5% castor oil, 0.8% D&C Red #7 Calcium Lake pigment, and 90.7% ethyl alcohol.

The rub test was designed to determine the test resin's ability to be retained on the skin. The composition used for the suspension test was painted on the skin and allowed to dry. Thereafter, the skin was rubbed under cool tap water until the composition began to fall apart. A composition received a score of "Good" if it was able to withstand five minutes or more of rubbing. A compound received a score of fair or poor if it withstood less than one minute of rubbing.

In the color test, the color of the resin containing compositions used in the suspension test was applied to the lips and the quality of the color obtained was compared to that produced using a composition lacking the test resin.

In the "feel on lips" test, the compositions used in the suspension test the compounds were evaluated to determine whether they produced a tight shrinking feeling, cracked, dried the lips, or caked on the lips. Compounds performing favorably in this test produced none of the preceding effects and were not noticeable to the wearer.

In the drying time test, the compositions used in the suspension test were applied to the lips and the length of time the composition took to dry was evaluated. Preferentially, the compositions take about 20 seconds to dry.

The above tests were performed on the following resins:
(1) Resin 28-2930 (VA/crotonates/vinyl neodecanoate copolymer) available from National Starch, Bridgewater, N.J.
(2) Amphomer LV-71 (octylacrylamide/acrylates/butylaminoethyl methacrylate copolymer) available from National Starch.
(3) Water Lock G40-A180-D242 (corn starch/acrylamide/sodium acrylate copolymer) available from Grain Processing Corp., Muscatine, Iowa 52761.
(4) Daihold (amp/acrylate copolymer) available from Sandoz Chemical Corp., Charlotte, N.C.
(5) Eastman AQ-385 and AQ-555 (Diglycol/cyclo hexanedimethanol/isophthalates/sulfylisophthates copolymer) available from Eastman Kodak, Rochester, N.Y.
(6) Ultra Hold 8 (acrylates/acrylamide copolymer) available from Base Corp., Clifton, N.J.
(7) Omnirez 2000 (2 butenedioic acid 2-monoethyl ester polymer with methoxyethene available from ISP, Sherman Oaks, Calif.
(8) Gantarez compounds such as A-425, ES 425, and ES-435 (which are butyl esters of PVM/MA copolymers), ES-335 (isopropyl ester of PVM/MA copolymer), or ES-225 and SP-215 (ethylesters of PVM/MA copolymer), all of which are available from ISP, Sherman Oaks, Calif.
(9) H2old EP-1 Terpolymer (Vinyl caprolactam/PVP/dimthylaminoethyl/methylacrylate copolymer) available from ISP, Sherman Oaks, Calif.
(10) Amphomer Lovocryl-47 (octylacrylamide/acrylates/butylaminoethyl methacrylate copolymer) available form National Starch, Bridgewater, N.J.
(11) Amphomer 28-4910 (octylacrylamide/acrylates/butylaminoethyl methacrylate copolymer) available form National Starch, Bridgewater, N.J.
(12) Advantage Plus terpolymer (VA/butylmaleate/isobomyl acrylate copolymer) available from ISP, Sherman Oaks, Calif.
(13) Copolymer 958 (PVP dimethylaminoethylmethacrylate copolymer) available from ISP, Sherman Oaks, Calif.
(14) Joncryl (styrene/acrylates copolymer available form SC Johnson Polymer, Racine, Wis.
(15) Sentry Polyvinyl acetate-12 (polyvinyl acetate) available from Union Carbide Corp,. Houston, Tex.
(16) Carboset-525 (acrylates copolymer) available from B.F. Goodrich, Brecksville, Ohio.

Table I summarizes the results of the performance tests.

Resin 28-2930, Amphomer LV-71, Amphomer Lovlocryl47, and Amphomer 28-4910 received an overall performance rating of "good" in the above performance tests. While any of the substances tested in the performance tests could be utilized in the formulation of the cosmetic of the invention, the alcohol soluble, water insoluble resin that serves as the film-forming agent preferably includes an AMPHOMER component. The most highly preferred AMPHOMER is Amphomer LV-71. In the preferred formulation the film-forming agent is preferably comprised of an AMPHOMER and ethyl cellulose.

AMPHOMER is a trademark under which copolymers of N-tert-octylacrylamide, methyl methacrylate, hydroxypropyl methacrylate, acrylic acid and t-butyl aminoethyl methacrylate are sold. GANTREZ is a trademark under which copolymers of vinyl methyl ether and mono-alkyl esters of maleic anhydride are sold by GAF. QUADAMER is a trademark under which terpolymers of alkyl acrylamide, acrylamide or methacrylamide, N-vinyl pyrrolidone and acrylic or methacrylic acid are sold by American Cyanamid. The most preferred film-forming agent is the commercially available AMPHOMER sold as LV-71 by National Starch and Chemical Company, Specialty Polymers, having an address of 10 Finderne Avenue, P.O. Box 6500, Bridgewater, N.J. 08007-3300.

The amphoteric acrylic resin forming the chemicals sold in the trade as AMPHOMER has previously been utilized as a fixture in hair spray as described, for example, in U.S. Pat. Nos. 4,192,861 and 4,315,910. However, Applicant has discovered that this substance can also serve as the preferred form of the critical ingredient of a cosmetic which forms a clear, colorless film on the lips and which has a staying power far greater than that of conventional lipsticks.

The AMPHOMER utilized in the cosmetic of the invention functions as a transparent sealer. It binds and seals the cosmetic to the lips in a clear, sheer film which does not crack or cake. The film-forming agent in the cosmetic composition is what makes the product so long lasting.

The AMPHOMER is an amphoteric acrylic resin. Its official Cosmetic Toiletries and Fragrances Association (CTFA) product designation is Octylacrylamide/Acrylates/Butylaminoethyl Methacrylate Copolymer. AMPHOMER is carboxylated at regular intervals along its molecular chain. In its undissolved form it is a fine white free-flowing powder. It has an intrinsic viscosity of 0.40 in ethanol at 25 degrees Centigrade. It contains about three percent volatiles and has an acidity of 2.05 me/gram.

The cosmetic of the invention contains no waxes or petroleum products. Waxes can smear while petroleum products can burn or dry the lips. The cosmetic of the invention is so sheer that a wearer can layer on at least three different layers without any danger of the product calling up on the lips. Indeed, the different layers of the cosmetic of the invention can be applied in different colors to achieve a unique, aesthetic effect Also, a different number of layers of the cosmetic can be applied to produce different aesthetic appearances. A single layer of the preferred embodiment of the cosmetic of the invention dries to a shear finish. If a second layer of the cosmetic is applied over the first, a medium matte finish is achieved. By applying a third layer, a wearer achieves a full cover matte finish. Even with use of multiple layers, however, the cosmetic of the invention will not cake, cake or smear.

The cosmetic of the invention can be formulated in any number of different colors by varying the color of the pigment employed. The cosmetic of the invention is in a liquid form when applied and the colors can be used individually or mixed by layering to create an unlimited array of custom, personalized colors. Each layer takes about twenty seconds to dry from the time of application.

In addition to its basic components, the cosmetic of the invention may include other substances to achieve certain effects. For example, the cosmetic may be formulated with at least about one part of a dimethicone component to achieve a gloss or satin effect. Although the cosmetic formulated in this manner looks and feels viscid or sticky, it will not come off, but will stay on the lips despite extended wear and exposure to moisture.

The cosmetic may also be formulated as a lip liner by utilizing a higher concentration of cosmetic dyes or pigments in the formulation. When formulated in this manner, the cosmetic may be utilized to outline the lips in the same or a different color as the basic application.

The cosmetic of the invention provides natural sun protection and keeps the lips from chapping, indoors or outdoors, in both cold and hot weather. It will not stick to teeth or dental braces. Unlike a user wearing lipstick, an individual wearing the cosmetic of the present invention can actually brush and floss after means without smearing the cosmetic or reducing the thickness of its lip coating, and without having to reapply the lip covering.

The cosmetic of the invention is organic and hypoallergenic. Unless a flavor or fragrance is added, it is also odor free and contains no petroleum products.

The cosmetic of the invention enhances the beauty of the wearer without surgery by filling in the inner lips where conventional lipstick will not stay. The cosmetic of the invention is extremely sheer and is not gooey like conventional lipstick. Even after three or more layers of the cosmetic of the invention are applied, the lips still fee bare and have a perfect matte finish.

The cosmetic of the invention is not at all viscous, and can even be poured from a container. Its sheer consistency allows it to be applied with a fine tip applicator so that it can be applied with the precision of a makeup artist.

The AMPHOMER utilized in the cosmetic of the invention functions as a transparent sealer. It binds and seals the cosmetic to the lips in a clear, sheer film which does not crack or cake. The film-forming agent in the cosmetic composition is what makes the product so long lasting.

The cosmetic of the invention will not come off with petroleum jelly or cleansing cream. Due to its permanence, care must be taken not to spill the cosmetic of the invention in liquid form onto clothing or other fabrics. However, if the cosmetic is accidentally spilled onto carpeting or clothing, it can be readily removed by applying water and then applying isopropyl alcohol or the cosmetic removing formulations described below, provided that cleanup is undertaken promptly.

To use the cosmetic of the invention, it is recommended that the lip area be cleaned thoroughly with the cosmetic removing compositions described below. A bottle of the cosmetic containing small mixing balls should be shaken for four or five times until the mixing balls move freely within the bottle.

The cosmetic of the invention is then applied generously in liquid form to dry, clean lips. It is recommended that three consecutive layers be applied at a time for full day-time coverage. The cosmetic can be applied with a soft doefoot applicator or brush applicator and should be applied across the lips in a single direction only. When applying the cosmetic, the wearer should keep in mind the freedom of creating fuller lips by filing in the inner lips where regular lipstick does not stay. Approximately 20 seconds should be allowed to elapse between consecutive coats in order to allow the immediately preceding coat to dry. During this time, the lips should be kept apart and not blotted. For best results after the application of the cosmetic of the invention, the wearer should refrain from eating, drinking or smoking for at least one minute.

With the application of the cosmetic, the wearer's lips will tingle at first. This tingling sensation diminishes or goes away entirely with repeated use, because the sealing effect of the product actually helps to eliminate the mild, but ever present chapping common to most lips.

The tingling sensation which is sometimes present may be avoided by applying at first a thin layer of the cosmetic containing dimethicone. Subsequent layers of the same or a different formulation of the cosmetic may be applied to achieve the desired degree of sheer or matte finish.

The bottle containing the cosmetic of the invention should be kept closed after each use. With daily use, a one quarter ounce bottle should last approximately two months.

As previously noted, the organic solvent or carner employed is preferably denatured alcohol, sometimes termed ethyl alcohol or ethanol. Other organic solvents which may be employed instead of or in addition to denatured alcohol include stearyl alcohol, cetyl alcohol, cetearyl-cetostearyl alcohol, SDA alcohol, methyl alcohol, isopropyl alcohol, isostearyl alcohol, laurel alcohol, myristyl alcohol, behenyl alcohol, synthetic alcohol and C18–40 alcohol. Other organic solvents which may be employed include higher fatty-acids which are immiscible in water. These include lauric acid, myristic acid, stearic acid, palmitic acid, behenic acid, and lanolin fatty acid. Lanolin and triterpene may also be employed in the organic solvent.

Depending upon the concentration of the other components, the organic solvent, which is preferably SDA 40B 190 denatured alcohol, is preferably present to the extent of between about 30 to 95 percent. Within this range, a concentration of 80 to 95 percent organic solvent will normally be utilized.

The pigments which are employed to provide the coloring to the cosmetic are normally provided as dispersions in castor oil. The pigment and castor oil are preferably present in the cosmetic of the invention in an aggregate amount of between about 0.1 percent and about ten percent. Pigments of this type are standardized in the cosmetic industry and are identified in that industry by FD&C designations, D&C designations, and natural color designations that are compatible with alcohol solutions. The preferred pigments that are employed include D&C Red No. 6, Barium Lake, D&C Red No. 7 Calcium Lake, D&C Orange No. 5, D&C Red No. 27, FD&C Yellow No. 5, FD&C Blue No. 1, iron oxide and others. The D&C lake colors are all made with iron, aluminum, calcium, barium, potassium, strontium or zirconium.

Other pigments which may be employed include those of dye or coal tar origin and chemical compounds used as pigments. Inorganic colors such as iron oxides may be utilized. White pigments may be formed of titanium dioxide, zinc oxide, mica or pearls. Pigments formed of nitro dyes may be utilized if desired. These dyes contain one atom of nitrogen and two of oxygen. However, only a few nitro dyes are certified by the FD&C or D&C because nitro dyes can be absorbed through the skin and some are toxic. However, D&C Yellow No. 5 is one acceptable nitro dye which can be used as a component of the pigment of the invention.

Azo pigments may also be utilized. These pigments are characterized by the presence of the azo bond, and monoazo pigments include the greatest number of pigments within this group.

Another group of suitable pigments is the triphenylmethane group. FD&C Blue No. 1 is the most popular dye of the group and is widely used in the cosmetic industry. Xanthene pigments may also be utilized. This group of pigments includes Berry brilliant, which is widely used in lipstick colors, as well as D&C orange.

Certain of the quinoline dyes are also suitable for use as pigments. There are only two certified cosmetic colors in this category, namely D&C Yellow Nos. 10 and 11. These are bright greenish yellow colors.

The anthraquinone dyes are also suitable for use in formulating the pigment required by the compositions of the invention. These dyes are widely used in cosmetics because they are not affected by light. D&C Violet No. 2 is one example of such a dye suitable for use in the invention. The anthrquinone dyes should not be used in the lip area, but may be used in other applications, such as on the nails.

Indigo dyes are also suitable for use and have been used in cosmetics for many years. D&C Blue No. 6 is one example of a suitable indigo dye.

Pigments of vegetable, animal, or mineral origin may also be utilized according to the invention. One suitable pigment of animal origin is cochineal extract. Natural colors and vegetable compound pigments which may be utilized include alkanet, annatto, carotene, chlorophyll, saffron and tumeric, beet juice powder, carmine, alkanet root, carmel, grape skin extract, and beta carotene. Hydroxyascetone and indelible dyes may also be utilized in formulating the pigment in the cosmetic of the invention.

The preferred embodiments of the cosmetic of the invention employ pigments of coloring dispersed in castor oil. This dispersion is present to the extent of between one percent and ten percent of the formulation. The degree of concentration of the pigments in caster oil determines the shade of the coloring. Normally a concentration of between 25–65 percent pigments in caster oil, in the aggregate, is employed in formulating the cosmetic. The castor oil acts like a plasticizer and also makes the film formed more flexible.

Alternatively, the pigments may be alcohol soluble pigments, such as D&C Red 28 Lake, in which case a castor oil dispersion is not necessary to solubilize the pigments in the present cosmetics.

The pigments may contain 0.1 to 5% stain. Preferably the pigment contains 0.65%–1.5% stain.

The alcohol soluble, water insoluble resin which is employed is the critical component that provides the cosmetic of the invention with its numerous advantages over lipstick. While AMPHOMER is preferably utilized as the requisite alcohol soluble, water insoluble resin, other may be used not only to add a white component of color, but also to serve as a sunscreen.

The cosmetic of the invention may also employ vitamins, minerals, antioxidants, drugs, organic compounds, herbs, proteins, currant extracts, root extracts, enzymes, sorbitol, pectin and PCA to take advantage of their known coloring, flavoring, moistening and adhering properties.

The invention may be further illustrated by way of the following examples.

EXAMPLE 1

The first step in formulating the cosmetic of the preferred embodiment of the invention is to create the sealer. The sealer is formed by mixing the film-forming agent in the organic solvent. Specifically, 4.4 parts of Amphomer LV-71, obtained from National Starch and Chemical Company, and 1.9 parts Ethocel N-22, obtained from Aqualon Corporation, are mixed at room temperature in 93.7 parts 190-proof specially denatured alcohol, sold as SDA 38B-190. The Ethocel N-22 provides ethyl cellulose which functions as an adjunct film former in the sealant. The sealer is then momentarily set aside.

Five parts by weight of a dispersion of D&C Red No. 7 Calcium Lake in castor oil and 0.5 parts by weight of a dispersion of D&C Orange No. 5 in castor oil are then selected for use as the pigment or coloring agent. Both the D&C Red No. 7 Calcium Lake and the D&C Orange No. 5 each comprise about 50 percent of the total weight of their respective dispersions. The remaining weight of the dispersions is attributable to the castor oil. The pigments should be obtained in as finely ground a form as possible. The pigment dispersions are mixed together along with another 0.5 parts by weight castor oil.

The pigment and castor oil mixture is then mixed in with the sealer, also at room temperature. The AMPHOMER, the Ethocel and the pigment ingredients are all readily soluble in the denatured alcohol. When mixed, the formulation forms a somewhat turbid solution. Pigment grinds can be stirred into the sealer in any convenient manner. The resultant liquid mixture is one preferred embodiment of a cosmetic according to the invention.

EXAMPLE 2

The formulation of Example 1 is repeated, but with the addition of two parts methyl silicone to the sealer prior to adding the pigments to the sealer. The use of a dimethicone such as methyl silicone increases the shininess of the cosmetic.

EXAMPLE 3

The formulation of Example 1 is repeated, but with the addition of two parts by weight of glycerin as a humectant in producing the sealer. The use of a humectant aids in moisturizing the lips.

EXAMPLE 4

A sealer is first prepared by mixing 4.3 parts by weight of Amphomer LV-71 along with 3.2 parts by weight Ethocell N-4 into 92.5 parts specially denatured alcohol SDA 40B-190. 8.25 parts of D&C Red No. 7 pigment dispersion in caster oil along with 0.25 parts D&C Orange No. 5 pigment dispersion in castor oil are then mixed with an additional 0.5 parts castor oil and introduced into the quantity of sealer previously prepared. The sealer, therefore, constitutes 90.75 parts by weight of the total composition. The pigment grinds and additional castor oil are stirred into the sealer to produce the finished liquid cosmetic composition according to the invention.

All of the formulations of the cosmetic of the foregoing examples will dry in a thin film, when applied to the lips. The cosmetic will not crack or cake even with repeated applications. When any of the foregoing formulations are applied to a wearer's lips in a least three layers, the cosmetic covering provided will last a wearer engaged in virtually any normal activity throughout an entire day without fading or rubbing off.

The above formulations may also be used to apply color to skin, nails, hair, or to cover bald spots. In addition, the above compositions can be used as liners to provide definition. For use as a liner, darker pigments are preferred, although any pigment will work. Additionally, if used as a liner, the composition should be applied to the lips with a fine tip brush.

Furthermore, with slight modifications, the above formulations may be used to apply color around the eyes. For application around the eyes, an aqueous solvent is used, the ethylcellulose is omitted, and Aminonathyl amino methyl propanol is added. A preferred composition for use around the eyes comprises between about 0.1 and about 20 parts of a water soluble resin, between about 0.1 and about 15 parts of a cosmetic pigment, between about 0.5 and about 4 parts Aminonathyl amino methyl propanol.

The present invention also contemplates compositions for enhancing the finish of the cosmetic. The composition can be applied over the cosmetic to enhance the matte finish of the cosmetic alone into a high-gloss finish In addition, the lips remain soft and silky while leaving the waterproof and smearproof cosmetic in place. The finish enhancing compositions may also be massaged lightly into the lips prior to application of the cosmetic to condition and moisturize the lips.

The finish enhancing composition comprises a silicone. Preferentially, the silicone is a silicone copolymer. in one version of this composition, the composition comprises about 100% silicone. The silicones function to provide a water barrier, gloss, and spreading and wetting activity. They may also include moisturizing abilities and may function as a carrier for other active ingredients such as sunscreens or vitamins. Mixtures of different silicones may also be used to achieve the desired moisturizing, carrier, or other beneficial effects. Virtually any of the silicones offered by GE Silicones will work in the present invention, including Cyclomethicone, Dimethicone, mixtures of the Cyclomethicone and Dimethicone, Dimethicone and Laureth-4 and Laureth-23, Dimethicone Copolyol, Cycomethicone and Dimethicone Copolyol, Trimethylsilylamodimethicone, and other silicones provided by GE Silicones for use in personal products. Preferentially, the silicone is a silicone copolymer. Preferred silicones are the Dimethicones available from GE Silicone and dimethylsiloxane methyl (polyoxytheylene) siloxane copolymer, such as the Dimethicone and Trimethylsiloxysilicate available from GE Silicones. Representative dimethicones include a polydimethylsiloxane having a viscosity of 5 centistokes at 25° C. such as SF96® (5), a polydimethylsiloxane having a viscosity of 20 centistokes at 25° C. such as SF96® (20), a polydimethylsiloxane having a viscosity of between 50 and 1000 centistokes at 25° C. such as SF96® (50–1000), a polydimethylsiloxane having a viscosity of 60,000 centistokes at 25° C. such as Viscasil® 60M, a blend of 15% of a high molecular weight methyl terminated polydimethylsiloxane fluid gum having a penetration between 500 and 1500 mm and 85% of a polydimethylsiloxane which has a viscosity of 5 centistokes at 25° C. such as SF1236, and a high molecular weight methyl terminated polydimethylsiloxane fluid gum having a penetration between 500 and 1500 mm such as SE30 all of which are available from GE Silicones.

In another version of this embodiment, the finish enhancing composition comprises a silicone, a lipophilic gelling agent and a preservative. The silicones suitable for use in this embodiment are the same as those for the composition above. The lipophilic gelling agent acts as a carrier for introducing additional components into the composition. Desirable additional components are discussed below. In a highly preferred embodiment, the lipophilic gelling agent is a cyclomethicone pentamer and aluminum magnesium hydroxide stearate such as Gilugel SIL-5 (produced by Giulini Chemie, Germany and available from Morse Chemical, Inc., San Gabriel, Calif.). A preferred preservative is phenoxyethanol. In a highly preferred version of the present invention, the finish enhancing composition comprises about 1 to about 99% silicone, about 0.1 to about 50% lipophilic gelling agent, and about 0.1 to about 10% preservative. In a highly preferred version the diinethylsioxane methyl (polyoxyethylene) siloxane copolymer is present at a concentration of 88.40%. In a highly preferred version, the Gilugel SIL-5 is present at 10%. Preferentially, the preservative is phenoxyethanol or BHT (butylated hydroxytoluene). In a preferred version, the phenoxyethanol is present at 1.6%. In another preferred embodiment, the BHT is present at 1.6%.

Additional components may be added to the above cornposition, including flavoring agents, slin conditioning agents, emollients, skin protectants, sunscreens, UV light absorbers, anti-oxidants, humectants, essential oils, minerals, PABA, hetrocyclic compounds, oils, fats, and fatty acids.

Representative flavoring agents which may be used in the present compositions include cinnamon, peppermint extract, saccharin, Acesulfame K and other flavoring agents such as those listed in the CTFA Cosmetic Ingredient Handbook 2d. ed., published by the cosmetic, Toiletry, and Fragrance Association, 1101 17th St. N.W., Suite 3000, Washington, D.C. 20036 (1992). The amounts and identities of such flavoring agents may be adjusted to provide a desirable flavor to the composition.

Numerous skin conditioning agents may be selected for use in the present compositions, provided they are oil soluble. These include the emollients, humectants, miscellaneous, and occlusive skin conditioning agents listed in the CTFA Cosmetic Ingredient Handbook. The amounts and identities of such skin conditioning agents can be adjusted to provide the desired results. A highly preferred humectant is glycerin. Many UV absorbing compounds are known to those skilled in the art, including those listed in the CTFA Cosmetic Ingredient Handbook. However, the preferred UV absorber is octylcrylene.

Numerous sunscreen agents are known to those skilled in the art, including those listed in the CTFA Cosmetic Ingredient Handbook. However, a preferred sunscreen is octyl methoxycinnamate. In a preferred version of this aspect, the antioxidant is a vitamin E linoleate mixture available from Seltzer Chemicals, Carlsbad, Calif.

Many skin protectants are known to those skilled in the art, including those listed in the CTFA Cosmetic Ingredient Handbook.

Many essential oils, minerals, PABA, heterocyclic compounds, oils, fats, and fatty acids suitable for use in the present compositions are known to those skilled in the art Representative compounds in each of these categories are listed in the CTFA Cosmetic Ingredients Handbook. Effective amounts of such compounds may be included in the present compositions to achieve the desired effect.

Preferred finish enhancing compositions are listed in Examples 5–8.

EXAMPLE 5

| AMOUNT (BY WEIGHT) | COMPOUND |
|---|---|
| 88.40 | Dimethylsiloxane methyl (polyoxyethylene) siloxane copolymer |
| 10.00 | Gilugel SIL-5 |
| 1.60 | Phenoxyethanol |

To formulate the above composition, the Gilugel SIL-5 is heated until it melts. The phenoxyethanol is then added thereto, and the resulting mixture is added to the the Dimethylsiloxane methyl (polyoxyethylene) siloxane copolymer.

EXAMPLE 6

| AMOUNT (BY WEIGHT) | COMPOUND |
|---|---|
| 7.00 | Dimethylsiloxane methyl (polyoxyethylene) siloxane copolymer |
| 5.50 | Gilugel SIL-5 |
| 0.30 | BHT (butylated hydroxytoluene) |
| 1.00 | Phenoxyethanol |
| 84.10 | Dimethicone |
| 1.00 | Octylcrylene |
| 1.00 | Octyl methoxycinnamate |
| .10 | Vitamin E linoleate mixture |

The composition is prepared by beating the Gilugel to the melting point and adding the octylcrylene, octyl methoxycinnamate, vitamin E, phenoxyethanol and BHT. The two silicones are separately mixed and the Gilugel mixture is then added thereto.

EXAMPLE 7

| AMOUNT (BY WEIGHT) | COMPOUND |
|---|---|
| 100.00 | Dimethicone |

EXAMPLE 8

| AMOUNT (BY WEIGHT) | COMPOUND |
|---|---|
| 100.00 | Dimethylsiloxane methyl (polyoxyethylene) siloxane |

The present invention also contemplates compositions for removing the cosmetic. One version of the cosmetic remover is a solution comprising a mild detergent plus a preservative. Preferentially, the mild detergent is present from between about 0.5 parts and about 10 parts and the preservative is present between about 0.1 and about 3 parts. A preferred mild detergent is sodium lauryl sulfate and a preferred preservative is Quaternium 15 (Dowicil 200 available from Dow Chemical) In a highly preferred embodiment of this composition, the sodium lauryl sulfate is present at 0.5 parts and the preservative is quatemium 15 (Dowicil 200 available from Dow Chemical) at 0.1 parts, with the remainder of the composition being water.

Altenatively, the lip removing composition may comprise a solution of alcohol and a chelating agent. In a preferred version of this embodiment, the alcohol is ethyl alcohol and the chelating agent is trisodium phosphate. Preferentially, the trisodium phosphate is present at about 0.1–5 parts by weight.

In yet another embodiment, the cosmetic removing composition comprises an aqueous solution of a chelating agent, one or more mild detergents, and a preservative. Preferentially, the water is distilled. Preferentially, the chelating agent is trisodium phosphate. Preferred mild detergents are Empigen CDR 30 (cocoampho acetate) available from Albright & Wilson, Cumbria, United Kingdom) and the nonionic surfactant polyoxyethylene poloxypropylene glycol (Pluronic® F127, Poloxamer 407). Preferred preservatives are phenoxyethanol, sodium benzoate, and Quaternium 15 (Dowacil 200 available from Dow Chemicals). In further aspects of this embodiment, one or more thickeners are added. A preferred thickener is xanthan gum. The xanthan gum also functions to maintain the solubility of sodium lauryl sulfate and trisodium phosphate in alcohol based formulations. In yet futher embodiments of the cosmetic removing composition a flavoring may be added. Preferred flavorings are Acesulfame K (a sweetener Sunnett Brand Sweetener available from Hoechst Celanes, 3340 W. Norfolk Rd, Portsmouth, Va. 23703), and sodium saccharin.

Preferentially, the chelating agent is present between about 0.5 and about 5 parts. It is preferred that the detergents be present from about 5.05 to about 20.5 parts. Preferentially the preservative is present between 0.1 and 5 parts. Preferentially, the thickener is present between about 0.05 and 10 parts. Preferentially the sweetener is present between about 0.05 and 5 parts.

Mild alkali solutions may also be used to remove the cosmetic. A preferred aspect of this embodiment is 0.5–5 parts sodium borate, with the remainder being water. In a highly preferred embodiment, the sodium borate comprises 1.78 parts of the aqueous solution.

Examples 9–15 describe highly preferred embodiments of the cosmetic removing formulations.

EXAMPLE 9

| AMOUNT (BY WEIGHT) | COMPOUND |
|---|---|
| 90.29 | DI water |
| 1.78 | Trisodium phosphate |
| .20 | Polyoxyethylene polyoxypropylene glycol (Poloxamer 407) |
| .13 | Acesulfame K |
| 1.60 | Phenoxyethanol |
| 6.00 | Cocoampho acetate (Empigen CDR 30) |

To formulate the above composition, trisodium phosphate, Poloxamer, Acesulfame K are first added to warm water. The cocoampho acetate is then added to this aqueous composition, followed by the addition of the phenoxyethanol.

The above formulation may also be used to remove coloring applied around the eyes.

EXAMPLE 10

| AMOUNT (BY WEIGHT) | COMPOUND |
|---|---|
| 80.67 | DI water |
| 16.25 | Ethanol (denatured with flavor) 190 proof |
| 1.25 | Trisodium phosphate |
| .25 | Xanthan gum |
| .20 | Polyoxyethylene polyoxypropylene glycol (Poloxamer 407) |
| .15 | Sodium lauryl sulfate |
| .13 | Sodium saccharin |
| 1.0 | Sodium benzoate |

To prepare the above formulation, trisodium phosphate, Poloxamer, sodium saccharine, sodium lauryl sulfate, and sodium benzoate are added to warm water. The xanthan gum is added separately to the alcohol. Next the alcohol mixture is added to the aqueous mixture. Finally, the glycerin is added to the above mixture.

Alternatively, the xanthan gum may be added to half of the water at room temperature. The trisodium phosphate, Poloxamer, sodium saccharin, sodium lauryl sulfate, and sodium benzoate may be added to warm water. The two aqueous mixtures may then be combined with the alcohol.

EXAMPLE 11

| AMOUNT (BY WEIGHT) | COMPOUND |
|---|---|
| 80.02 | DI water |
| 16.25 | Ethanol (denatued with flavor) 190 proof |
| 1.25 | Trisodium phosphate |
| .25 | Xanthangum |
| .20 | Polyoxyethylene polyoxypropylene glycol (Poloxamer 407) |
| .30 | Glycerin |
| .13 | Sodium saccharin |
| 1.60 | Phenoxyethanol |

To formulate the above composition, the trisodium phosphate, sodium saccharine, phenoxyethanol, and Poloxamer are added to warm water. The xantham gum is separately mixed with the alcohol. The alcohol mixture is then combined with the aqueous mixture and the glycerin is added thereto.

Alternatively, the xanthan gum may be added to half of the water at room temperature. The trisodium phosphate, sodium saccharine, phenoxyethanol, and Poloxamer are added to warm water may be added to warm water. The two aqueous mixtures may then be combined with the alcohol.

EXAMPLE 12

| AMOUNT (BY WEIGHT) | COMPOUND |
|---|---|
| 90.30 | DI water |
| 1.78 | Trisodium phosphate |
| .20 | Polyoxyethylene polyoxypropylene glycol (Poloxamer 407) |
| 6.00 | Cocoampho acetate (Empigen CDR 30) |
| .12 | Sodium saccharin |
| 1.60 | Phenoxyethanol |

To formulate the above composition, the trisodium phosphate, sodium saccharine, phenoxyethanol, and Poloxamer are added to warm water. The xantham gum is separately mixed with the alcohol. The alcohol mixture is then combined with the aqueous mixture and the glycerin is added thereto. Finally, the cocoampho acetate is added thereto.

The above formulation may also be used to remove color applied around the eyes.

EXAMPLE 13

| AMOUNT (BY WEIGHT) | COMPOUND |
|---|---|
| 91.69 | DI water |
| 1.78 | Trisodium phosphate |
| .20 | Polyoxyethylene polyoxypropylene glycol (Poloxamer 407) |
| 6.00 | Cocoampho acetate (Empigen CDR 30) |
| .13 | Acesulfame K |
| .20 | Quaternium 15 |

To formulate the above composition, the Quaternium 15 is first added to the water. The Poloxamer, trisodium phosphate, and Acesulfame K are then added thereto. Finally, the cocoampho acetate is added thereto.

EXAMPLE 14

| AMOUNT (BY WEIGHT) | COMPOUND |
|---|---|
| 0.5 | Sodium lauryl sulfate |
| 90.3 | Distilled water |
| 0.2 | Quaternium 15 |

EXAMPLE 15

| AMOUNT (BY WEIGHT) | COMPOUND |
|---|---|
| 1.78 | Trisodium phosphate |
| 98.22 | Ethyl alcohol |

The compositions of Examples 12 and 13 are highly preferred.

The present invention also relates to compositions for further enhancing the color of the cosmetic. These color enhancing compositions comprise colorants such as mica, bismuth oxychloride, iron oxides, D&C Lake colorants, FD&C Lake colorants, D&C colorants, and FD&C colorants. The color enhancing compositions are provided in pressed or loose form. If provided in pressed form, the colorants are mixed with preservatives. Preferred preservatives are ethyl paraben, methyl paraben, or polyparaben. Additionally if provided in the pressed form, a the color enhancing composition also comprises a wax such as corn glutin protein or a synthetic wax and as C12–C15 alkyl benzoate.

A preferred formulation for enhancing the color of the cosmetic is described in Example 16.

EXAMPLE 16

| AMOUNT (BY WEIGHT) | COMPOUND |
|---|---|
| 4.24 | Zinc Stearate |
| 3.74 | Bismuth oxychloride |
| 66.03 | Colored mica powder |
| 14.95 | C12–C15 alkyl benzoate |
| 8.72 | Synthetic wax/ corn glutin protein mixture from Presperse, Inc., 601 Hadley Rd., South Plainfield, NJ 07080 |
| 1.3 | Ethylparaben |
| 0.65 | Methylparaben |
| 0.15 | Propylparaben |

To press the above composition, the loose powder is first blended in an industrial blender. The resulting composition is thereafter placed in a press.

Undoubtedly, numerous variations and modifications of the invention will become readily apparent to those familiar with cosmetic products. Accordingly, the scope of the invention should not be construed as limited to the specific examples described, as those examples are presented herein only as being illustrative of the many formulations possible according to the invention.

TABLE I

| Compound Number | Suspension Test | Color Test | Rub Test | Drying Time | Feel on Lips | Overall Performance | Notes |
|---|---|---|---|---|---|---|---|
| 1 Resin 28-2930 | Good | Good | Good | Good | Fair | Good | Versatile but can shrink/dry on lips |
| 2 Amphomer LV-71 | Good | Good | Good | Good | Good | Good | Best resin (most preferred) |
| 3 Water Lock G40-A180-D242 | Fair | Fair | Poor | Fair | Poor | Poor | Creates nice film but too grainy |
| 4 Daihold | Fair | Poor | Fair | Poor | Fair | Fair | Similar to Amphomer |
| 5 Eastman AQ-385 and AQ-555 | Fair | Fair | Fair | Fair | Fair | Fair | Similar to Amphomer |
| 6 Ultra Hold 8 | Fair | Poor | Poor | Fair | Fair | Fair | Similar to Amphomer |
| 7 Omnirez 2000 | Good | Poor | Fair | Good | Good | Fair | Creates good film but poor color |
| 8 Gantarez compounds | Poor | Poor | Poor | Fair | Poor | Poor | Burns lips, poor performance in rub test |
| 9 H2old EP-1 Terpolymer | Fair | Poor | Poor | Good | Fair | Fair | Very sheer, does not hold color well, felt good on lips and could |

TABLE I-continued

| Compound Number | Suspension Test | Color Test | Rub Test | Drying Time | Feel on Lips | Overall Performance | Notes |
|---|---|---|---|---|---|---|---|
| | | | | | | | be added to amphomer to strengthen hold |
| 10 Amphomer Lovocryl-47 | Good | Good | Good | Good | Good | Good | Good in every respect but does not last as long on lips and in rub tests |
| 11 Amphomer 28-4910 | Good | Good | Fair | Good | Good | Good | Does not last as long in rub tests |
| 12 Advantage Plus terpolymer | Fair | Poor | Poor | Good | Poor | Fair | Causes puckering of lips; too tight, too firm to pass rub tests; comes off in patches on lips; dries quickly; aids in a tack free feeling on lips |
| 13 Copolymer 958 | Poor | Poor | Fair | Good | Poor | Poor | Tacky on lips; transparent color; too thin; resin may be too firm |
| 14 Joncryl | Poor | Fair | Poor | Good | Fair | Fair | Burned lips; transparent color; doesn't pass rub test; dried quickly; left sediment in bottom of solution |
| 15 Sentry Polyvinyl acetate-12 | Poor | Poor | Poor | Poor | Fair | Poor | Hard to work with in adding other ingredients, slow drying time, sticky on lips |
| 16 Carboset-525 | Fair | Poor | Fair | Poor | Fair | Fair | |

What is claimed is:

1. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;
   wherein said liquid lip coloring comprises between about 0.1 and about 20 parts of the alcohol soluble and water insoluble resin, between about 0.1 and about 15 parts of the cosmetic pigment, and between about 50 and 99 parts of the organic solvent.

2. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;
   wherein said moisturizing gloss further comprises a lipophilic gelling agent.

3. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;
   wherein said silicone is a dimethicone copolymer.

4. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;
   wherein said silicone is selected from the group consisting of Cyclomethicone, mixtures of Cyclomethicone and Dimethicone, Dimethicone and Laureth-4 and Laureth-23, Dimethicone Copolyon, Cycomethicone and Dimethicone Copolyon, and Trimethylsilylamodimethicone.

5. The method of claim 3, wherein said dimethicone copolymer comprises Dimethicone and Trimethylsiloxysilicate.

6. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;
   wherein said silicone is dimethylsiloxane methyl (polyoxyethylene) siloxane copolymer.

7. The method of claim 2, wherein said lipophilic gelling agent comprises a cyclomethicone pentamer and aluminum magnesium hydroxide stearate.

8. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;
   said method further comprising applying a cosmetic removing solution when it is desired to remove said cosmetic from the lips.

9. The method of claim 8, wherein said cosmetic removing solution comprises an alcohol.

10. The method of claim 8, wherein said cosmetic removing solution comprises a detergent.

11. The method of claim 8, wherein said removing solution is applied as a liquid.

12. A method of coloring the lips comprising:
   a. applying a liquid lip coloring to the lips, said liquid lip coloring comprising an alcohol soluble and water insoluble resin, a cosmetic pigment, and an organic solvent; and b. applying a moisturizing gloss to the lips, said moisturizing gloss comprising a silicone;

wherein said alcohol soluble and water insoluble resin is an acrylate/octylacrylamide copolymer and said silicone is a dimethicone.

13. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;

wherein said alcohol soluble and water insoluble resin is an acrylate copolymer and said silicone is dimethicone.

14. A method of coloring the lips comprising:
   a. applying a liquid lip coloring to the lips, said liquid lip coloring comprising an alcohol soluble and water insoluble resin, a cosmetic pigment, and an organic solvent; and
   b. applying a moisturizing gloss to the lips, said moisturizing gloss comprising a silicone;

wherein said alcohol soluble and water insoluble resin is an acrylamide copolymer and said silicone is a dimethicone.

15. A method of applying and removing a lip coloring to and from lips, said method comprising:

a. applying a liquid lip coloring to the lips, said liquid lip coloring comprising an alcohol soluble and water insoluble resin, a cosmetic pigment, and an organic solvent;
   b. applying a moisturizing gloss to the lips, said moisturizing gloss comprising a silicone; and
   c. removing said lip coloring by applying a remover to the lips, said remover comprising an alcohol.

* * * * *